United States Patent [19]

Quarles

[11] Patent Number: 5,776,920
[45] Date of Patent: Jul. 7, 1998

[54] METHOD FOR TREATMENT OF PSORIASIS

[76] Inventor: Ruth Quarles, 1306 Karen Oval, Vienna, Ohio 44473

[21] Appl. No.: 510,389

[22] Filed: Aug. 2, 1995

[51] Int. Cl.$^6$ .................... A61K 31/615; A61K 31/19; A61K 31/17
[52] U.S. Cl. .................... 514/162; 514/557; 514/588
[58] Field of Search .................... 514/162, 588, 514/557

[56] References Cited

U.S. PATENT DOCUMENTS

| | | | |
|---|---|---|---|
| 4,007,271 | 2/1977 | Robertson | 424/234 |
| 4,194,007 | 3/1980 | Van Scott et al. | 424/318 |
| 4,483,854 | 11/1984 | Diamond | 424/230 |
| 4,512,978 | 4/1985 | Inwood | 424/145 |
| 4,551,480 | 11/1985 | Stiefel et al. | 514/680 |
| 4,569,935 | 2/1986 | Rosenberg et al. | 514/252 |
| 4,740,372 | 4/1988 | Boncic | 424/94.64 |
| 4,767,750 | 8/1988 | Jacquet et al. | 514/159 |
| 4,769,390 | 9/1988 | Roelz et al. | 514/588 |
| 4,826,677 | 5/1989 | Mueller et al. | 424/78 |
| 4,868,219 | 9/1989 | Thornfeldt | 514/663 |
| 4,892,888 | 1/1990 | Grollier et al. | 514/132 |
| 4,915,973 | 4/1990 | Costa | 424/667 |
| 4,981,681 | 1/1991 | Tosti | 424/78 |
| 5,004,736 | 4/1991 | Visnjic | 514/161 |
| 5,045,559 | 9/1991 | Scott | 514/423 |
| 5,061,486 | 10/1991 | Whitefield | 424/81 |
| 5,104,877 | 4/1992 | Boger | 514/256 |
| 5,122,536 | 6/1992 | Perricone | 514/474 |
| 5,165,932 | 11/1992 | Horvath | 424/195.1 |

OTHER PUBLICATIONS

Medical Journal of Australia, vol. 152, p. 158 (Feb. 5, 1990).
Compendium of Drug Therapy (1990).
Lowe, N.J., "Practical Psoriasis Therapy", Published by Year Bood Medical Publishers, Inc., pp. 28–39, 1986.

*Primary Examiner*—Raymond Henley, III
*Attorney, Agent, or Firm*—Bryan Cave LLP

[57] ABSTRACT

A preparation containing salicylic acid, lactic acid and urea in a moisturizing base, which can be used for the topical treatment of psoriasis.

20 Claims, No Drawings

METHOD FOR TREATMENT OF PSORIASIS

FIELD OF THE INVENTION

This invention relates to a composition for the treatment of psoriasis, a process for preparing the composition, and a method of treating psoriasis using the composition.

BACKGROUND OF THE INVENTION

Psoriasis is a condition characterized by hyperproliferation of skin above an erythematous base. The disorder has a rapid turnover and greatly increased production of epidermal cells with lichenification and shedding. Dilated capillaries underlie these scales, producing the erythematous base. This multifactorial condition, known for remissions and recurrences, has no known cure. The disorder can affect any area of skin, but primarily affects the extensor surfaces of the knees, elbows, knuckles, scalp, and buttocks. Psoriasis is characterized by severe itching, scaling, bleeding with scratching and trauma, and infection. The disorder often results in severe embarrassment.

Currently available treatments are generally directed towards reducing the rate of cell growth; keratolysis; anti-inflammatory action; inhibition of prostaglandin production; and inhibition of DNA synthesis. The most frequently used medications are corticosteroids, tar preparations, ultraviolet light treatments and systemic drugs.

SUMMARY OF THE INVENTION

One object of this invention is to provide an inoffensive, topical composition for the treatment of psoriasis.

A further object of this invention is to provide a composition for the treatment of psoriasis which contains no corticosteroid or other systemically toxic ingredient.

A further object of this invention is to provide an improved method for treating psoriasis.

Additional objects of this invention are to relieve the persistent itch experienced in this condition, and to reduce the scale production by its keratolytic action.

These objects are achieved by the use of a composition for the treatment of psoriasis which comprises from about 5% to about 40% by weight of salicylic acid, from about 1% to about 20% by weight of urea, and from about 0.5% to about 20% by weight of lactic acid. In a preferred embodiment, the composition comprises from about 10% to about 20% by weight of salicylic acid, from about 8% to about 15% by weight of urea, and from about 1% to about 5% by weight of lactic acid. In a more preferred embodiment, the composition comprises from about 10% to about 15% by weight of salicylic acid, about 8% to about 10% by weight of urea dissolved in water, and about 3% to 5% by weight of lactic acid.

DETAILED DESCRIPTION OF THE PREPARATION

Preferably the ingredients of the composition are contained in a hydrophilic cream which is compatible with most acid or alkaline substances. A preferred cream is known as Velvachol, which is marketed by Galderma Labs, Inc. of Fort Worth, Tex. Velvachol is a neutral, hydrophilic cream which contains water, petrolatum, mineral oil, cetyl alcohol, stearyl alcohol, sodium lauryl sulfate, cholesterol, methylparaben, butylparaben, and propylparaben.

The composition may also contain additional, conventional moisturizers, such as glycerine and mineral oil. A preferred moisturizer is glycerine. The composition preferably contains from 1% to 20% by weight of moisturizer, more preferably from 5% to 15% by weight.

Other conventional ingredients, such as fragrances and coloring agents, may also be included, generally in amounts from 1% to 15% by weight.

The composition may be prepared by mixing the ingredients together so that they form a smooth cream. The mixing may be done either by hand or with a mechanical mixer, such as one available to a pharmacist. Preferably, the composition is prepared by first mixing salicylic acid powder with glycerine to form a smooth mixture. The hydrophilic cream is then added, followed by the lactic acid. The composition is then mixed well. Finally, a solution of urea in water is added. The entire composition is thoroughly mixed, and should be stored in an air tight container.

Treatment of psoriasis using the composition is accomplished by topical application of the composition to the affected areas of skin two or three times a day for the first one or two weeks. The composition should be applied in such a manner as to lightly coat the affected skin area and the cream is then smoothed into the skin until absorbed. After one or two weeks, the composition is applied daily as needed to control itch and scale. As satisfactory control is obtained, use may decrease.

While not wishing to be limited by any particular theory, it is believed that the preparation effects a resolution of the condition by relieving the puritis, keratolysis of lichenified skin, and allowing the resolution of capillaries underneath the lichenified skin. It is believed that the preparation also moisturizes the skin underlying the scale to enact atrophy of the dilated capillaries and clearing of the skin.

The following examples are intended to illustrate the invention without, however, being of a limiting nature.

EXAMPLE 1

Preparation of the composition

Twenty-four grams of urea were dissolved in 50 cc of distilled water and set aside. Twenty-four grams of salicylic acid power was triturated with 24 cc of glycerine to form a smooth mixture. A hydrophilic cream (velvachol) was added to form a total volume of 240 cc. To this mixture 7.2 cc of lactic acid were added, and the composition was mixed well. The urea solution was added to this mixture. The composition was again thoroughly mixed. Approximately 240 cc of the composition were obtained, having the following formulation (all percentages are by weight):

10% urea
10% glycerine
3% lactic acid
10% salicylic acid
67% velvachol

EXAMPLE 2

Preparation of the composition

Example 1 was repeated except that 36 grams of salicylic acid powder were used. The composition had the following formulation (all percentages are by weight):

10% urea
10% glycerine
3% lactic acid
15% salicylic acid
62% Velvachol

CLINICAL RESULTS

The following examples describe the results observed in patients who have used the composition of the invention. In each case the patient was given a composition prepared as described in Examples 1 or 2 and instructed to apply it to the affected areas and smooth it into the skin until the cream had been absorbed. If the hands were not affected by psoriasis, the patients were instructed to wash their hands, since the composition may cause irritation to non-affected areas.

EXAMPLE 3

33 year old white female

Prior treatment history—Patient had an 11-year history of psoriasis (per medical record) on legs, back, elbows and knees, and had been treated previously with a steroid preparation and Balnatar. She reported a recurrence of lesions which had been present for approximately 18–24 months. The lesions were dry and scaly with a white surface and erythematous base.

Results (using composition of Example 1)—She had almost complete resolution while using the composition of the invention. She stopped using it when she ran out about 4 months later, and the lesions then returned to the pre-treatment state.

EXAMPLE 4

60-year old white female

Prior treatment history—Patient had a 10-year history of psoriasis (per medical record) on elbows, knuckles and fingernails, and had been using Lidex for 3–4 years, then Fototar & Estar. She had also previously used fish oil, which helped more than Lidex, as well as Diprolene ointment and 5% Salacid with 5% LCD, a tar preparation, in combination with Diprolene. She was seen by dermatologist when lesions spread to ankles, toes and trunk and continued on Salacid, then LCD in Nivea, followed by Temovate, a steroid, and Dovonex. She experienced little or no improvement with most medications.

Results (using composition of Example 1)—Scales went away, the skin became erythematous. Her skin never itched.

EXAMPLE 5

46-year old white male

Prior treatment history—11 year history of psoriasis, which was diagnosed by a dermatologist using a biopsy. He was given a prescription at that time of U.V. light, antibiotics, Atarax, Lidex mixed with aqua lacten. He developed reaction to U.V. light & was changed to Chlortrimenton. There was improvement, but the psoriasis flared again after a course of treatment for a smashed thumb with Keflex and Vicodin. He suspended treatment and was seen by another dermatologist. Five years later with an acute flareup, he was prescribed U.V. light and Fototar and remissions achieved in approximately one month. Three months later more lesions started, with a full recurrence four years later. He was again treated with prototherapy. All areas resolved but sacral area of back. He also developed basal cell cancer possibly from exposure of U.V. treatment. There was a recurrence of psoriasis in three months. He requested another dermatologist referral, and was prescribed Psorcon ointment; he was also told that if Psorcon did not help U.V. treatments would be needed. The usual course for U.V. treatment is 20 treatments (5 times a week for 4 weeks.)

Results (using composition of Example 1)—Patient was seen 7 months after using beginning use of the composition of the invention; at that time the psoriasis was completely gone.

EXAMPLE 6

50-year old white male

Prior treatment history—Forty-seven year history of psoriasis on knees and elbows. Had UV treatment in the 1970's, and was seen again by a dermatologist in late 1980's and treated with Temovate cream and natural sunlight, Triamcinolone cream and Kenalog injections under the placques. He showed some improvement, but stopped seeing dermatologist because he did not like using steroids. He received off and on treatment with Temovate for flareup with improvement.

Results—He used the composition of Example 1 (containing 10% by weight of salicylic acid) for three months. Then he switched to the composition of Example 2 (containing 15% by weight of salicylic acid). He experienced complete resolution of placque, erythematous and itch. However, the itch resumed when the composition was not used for 3–4 day periods.

EXAMPLE 7

46-year old white female

Prior treatment history—11 year history of psoriasis. Seen by dermatologist and given Diprolene lotion, Lidex cream and Anthralin. No record of response to this treatment.

Results (using composition of Example 1)—She had resolution of itch and white scale.

EXAMPLE 8

76-year old white male

Prior treatment history—Patient had arthritis for many years and psoriasis for 50 years and skin lesions. He was diagnosed with psoriatic arthritis, and treated by with Kenalog cream by his primary care physician. His arms and legs were heavily involved, but he denied itching.

Results (using composition of Example 2)—Patient applied small amounts of the composition to affected areas. He noticed some improvement to scaling.

EXAMPLE 9

41-year old white female

Prior treatment history—History of rheumatoid arthritis for many years, then developed a raised red rash. Seen by rheumatologist and diagnosed with psoriatic arthritis. Used Placquenil, and Prednisone daily, as well as topical treatment UVB. Experienced multiple improvements, brief remissions and flareups.

Results (using composition of Example 1)—She was not seen in follow up. There was apparently little improvement and psoriasis remains severe problem.

EXAMPLE 10

43-year old female

Prior treatment history—More than a ten-year history of psoriasis to knees and elbows. She had been treated in past with Lidex but there was no indication that she had ever seen dermatologist. She had experienced remissions and flares, especially with stress.

Results (using composition of Example 1)—Itch completely disappeared. The skin was still erythematous.

EXAMPLE 11

22 year old male

Prior treatment history—Patient had a long history of ichthyosis since age nine; he had been treated with moisturizers, but had not seen by dermatologist. There was a patch of psoriasis on his right elbow, which is periodically itchy.

Results (using composition of Example 1)—Patient used cream for two weeks and ran out. Some improvement in scale was noticed.

EXAMPLE 12

43-year old female

Prior treatment history—Patient has had a skin rash for more than 30 years, she claims since birth. Psoriasis was diagnosed by biopsy. She had been treated with Lidex and Triamcinolone and antihistamines for lesions on elbow, forearms and scalp.

Results (using composition of Example 2)—Patient states cream is helpful if used daily. States she uses with hydrocortisone for itching.

EXAMPLE 13

53-year old

Prior treatment history—Patient had a rash of 3 months duration, and had very itchy lesions over most of body. Had been seen by dermatologist for a similar rash in past. Results (using composition of Example 2)—Patient had significant improvement in scale and itch on area after one week. Diagnostic biopsy consistent with lichen planus, a skin condition which resembles psoriasis but which may be treated with an antibiotic. Patient continued using cream because of improvement, and was started on Grifulvin antibiotic.

EXAMPLE 14

77-year old white male

Prior treatment history—Patient had more than a twelve-year history of psoriasis which started on hands worked its way up his arms. He tried steroid cream, without improvement. He was referred to dermatologist; a biopsy was diagnostic of psoriasis. He was treated with Lidex, antihistamines and antibiotics without improvement. Was given intralesional Depo Medol and change to Halog ointment by his primary care physician with improvement for 3 months. Referred to another dermatologist for rash on hands, arms and knees. Had UVB treatment with good response. Two years later patient developed an eruption on hands and diagnosed with lichen simplex chronicus which was treated with Temovate and Topicort. Psoriasis was stable for two years and then flared. Patient was given PUVA treatment with marked improvement for one and a half months. Now has psoriasis over 80% of body.

Results (using composition of Example 2)—Noted improvement in scale and itch, even daughter remarked skin was better on medication. Used for one week when his primary care physician referred him to another dermatologist.

EXAMPLE 15

30-year old white male

Prior treatment history—Patient had psoriasis on elbows for an unspecified period of time.

Results (using composition of Example 2)—Itch was eliminated.

EXAMPLE 16

49-year old black male

Prior treatment history—Patient had an eight-year history of psoriasis on knees. Used body lotions and creams to decrease scale.

Results (using composition of Example 2)—Complete resolution of itch and scale within 1 month.

I claim:

1. A method for the treatment of psoriasis comprising the application of an effective amount of a composition comprising:

(a) from about 10% to about 40% by weight of salicylic acid, (b) from about 1% to about 20% by weight of urea, and (c) from about 0.5% to about 20% by weight of lactic acid; the composition being applied at least once per day for a period of at least 4 days.

2. The method according to claim 1, wherein the salicylic acid, the urea, and the lactic acid are contained in a hydrophilic cream.

3. The method according to claim 1, wherein the composition comprises from about 10% to about 20% salicylic acid by weight, from about 8% to about 15% urea by weight, and from about 1% to about 5% lactic acid by weight.

4. The method according to claim 1, wherein the composition further comprises from 1-20% by weight of a moisturizer selected from the group consisting of glycerine, mineral oil, and mixtures thereof.

5. The method according to claim 4, wherein the moisturizer is glycerine.

6. The method according to claim 1, wherein the composition is prepared by a process comprising mixing together salicylic acid, lactic acid, urea, and other ingredients, in amounts such the total amount of salicylic acid used in the preparation is from about 10% to about 40% by weight with respect to the entire composition, the total amount of lactic acid used in the preparation is from about 0.5% to about 20% by weight with respect to the entire composition, and the total amount of urea used in the preparation is from about 1% to about 20% by weight of the entire composition.

7. The method according to claim 1, wherein the composition is applied at least two times per day.

8. The method according to claim 6, wherein the composition is applied at least two times per day.

9. The method according to claim 1, wherein the composition is prepared by a process comprising mixing together salicylic acid, lactic acid, urea, and other ingredients, in amounts such the total amount of salicylic acid used in the preparation is from about 10% to about 20% by weight with respect to the entire composition, the total amount of lactic acid used in the preparation is from about 1% to about 5% by weight with respect to the entire composition, and the total amount of urea used in the preparation is from about 8% to about 15% by weight of the entire composition.

10. The method according to claim 9, wherein the composition is applied at least two times per day.

11. A method for the treatment of psoriasis comprising the application of an effective amount of a composition comprising:

(a) from about 10% to about 40% by weight of salicylic acid, (b) from about 1% to about 20% by weight of urea, and (c) from about 0.5% to about 20% by weight of lactic acid;

the composition being applied at least once per day for a period of at least one week.

12. The method according to claim 11, wherein the salicylic acid, the urea, and the lactic acid are contained in a hydrophilic cream.

13. The method according to claim 11, wherein the composition comprises from about 10% to about 20% salicylic acid by weight, from about 8% to about 15% urea by weight and from about 1% to about 5% lactic acid by weight.

14. The method according to claim 11, wherein the composition further comprises from 1-20% by weight of a moisturizer selected from the group consisting of glycerine, mineral oil, and mixtures thereof.

15. The method according to claim 14, wherein the moisturizer is glycerine.

16. The method according to claim 11, wherein the composition is prepared by a process comprising mixing together salicylic acid, lactic acid, urea, and other ingredients, in amounts such the total amount of salicylic acid used in the preparation is from about 10% to about 40% by weight with respect to the entire composition, the total amount of lactic acid used in the preparation is from about 0.5% to about 20% by weight with respect to the entire composition, and the total amount of urea used in the preparation is from about 1% to about 20% by weight of the entire composition.

17. The method according to claim 11, wherein the composition is applied at least two times per day.

18. The method according to claim 16, wherein the composition is applied at least two times per day.

19. The method according to claim 11, wherein the composition is prepared by a process comprising mixing together salicylic acid, lactic acid, urea, and other ingredients, in amounts such the total amount of salicylic acid used in the preparation is from about 10% to about 20% by weight with respect to the entire composition, the total amount of lactic acid used in the preparation is from about 1% to about 5% by weight with respect to the entire composition, and the total amount of urea used in the preparation is from about 8% to about 15% by weight of the entire composition.

20. The method according to claim 19, wherein the composition is applied at least two times per day.

* * * * *